United States Patent
Hilfinger et al.

[11] Patent Number: 5,862,558
[45] Date of Patent: Jan. 26, 1999

[54] BRUSH SECTION FOR AN ELECTRIC TOOTHBRUSH

[75] Inventors: Peter Hilfinger, Bad Homburg; Karl Herzog, Frankfurt; Gerhard Kressner, Altenstadt, all of Germany

[73] Assignee: Braun Aktiengesellschaft, Frankfurt, Germany

[21] Appl. No.: 823,413

[22] Filed: Mar. 25, 1997

[30] Foreign Application Priority Data

Oct. 29, 1994 [DE] Germany .............................. 44 38 732

[51] Int. Cl.⁶ ............................ A61C 17/34; A46B 13/02
[52] U.S. Cl. ................................................ 15/28; 15/22.1
[58] Field of Search .................................... 15/22.1, 22.2, 15/22.4, 28, 23, 29; 433/216

[56] References Cited

U.S. PATENT DOCUMENTS 5,416,942  5/1995  Baldacci et al. ............................ 15/28

FOREIGN PATENT DOCUMENTS 39 31 982  4/1991  Germany .
39 37 850  5/1991  Germany .
42 39 251  5/1994  Germany .
WO94/12121  6/1994  WIPO .

OTHER PUBLICATIONS

Copy of International Search Report dated Nov. 29, 1995.

Primary Examiner—Gary K. Graham
Attorney, Agent, or Firm—Fish & Richardson P.C.

[57] ABSTRACT

The invention is directed to a brush section (1) for an electric toothbrush which includes a mounting tube (2) in which a shaft (7) rotary about a longitudinal axis (3) is received. Further, the brush section (1) includes a bristle carrier (11) from which bristles (15) extend in the direction of a brush axis (14). The bristle carrier (11) is rotary about a transverse axis (19) by means of a bearing pin (21). By means of in particular a tapered disk (24), the brush axis (14) and the transverse axis (19) define between them an angle (28) departing from an apex (29). In operation of the electric toothbrush, the bristle carrier (11) performs a nutating motion about the transverse axis (19). This effects a revolving approaching/receding motion of the free ends of the bristles (15) resulting in an improved cleaning action on a user's teeth.

29 Claims, 7 Drawing Sheets

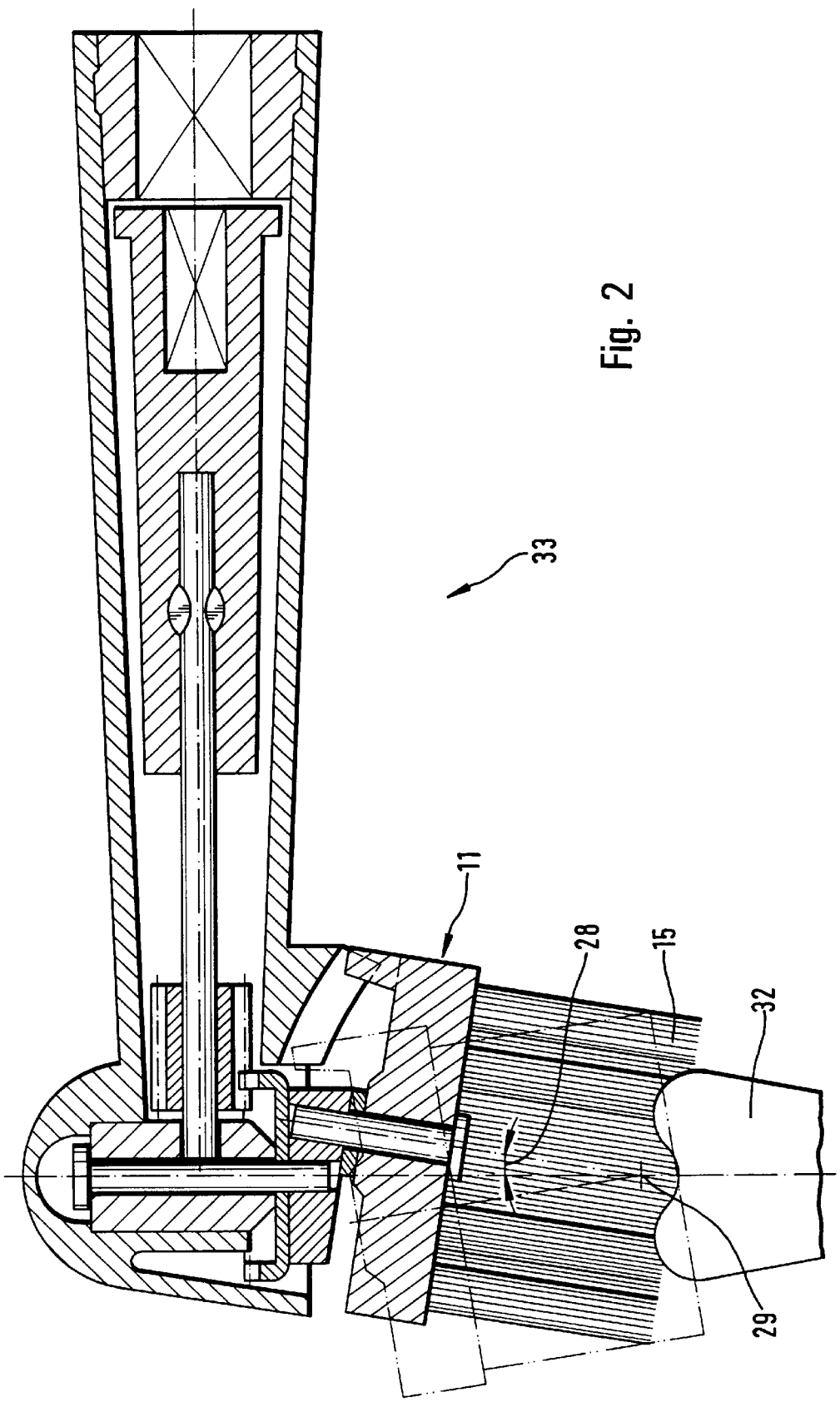

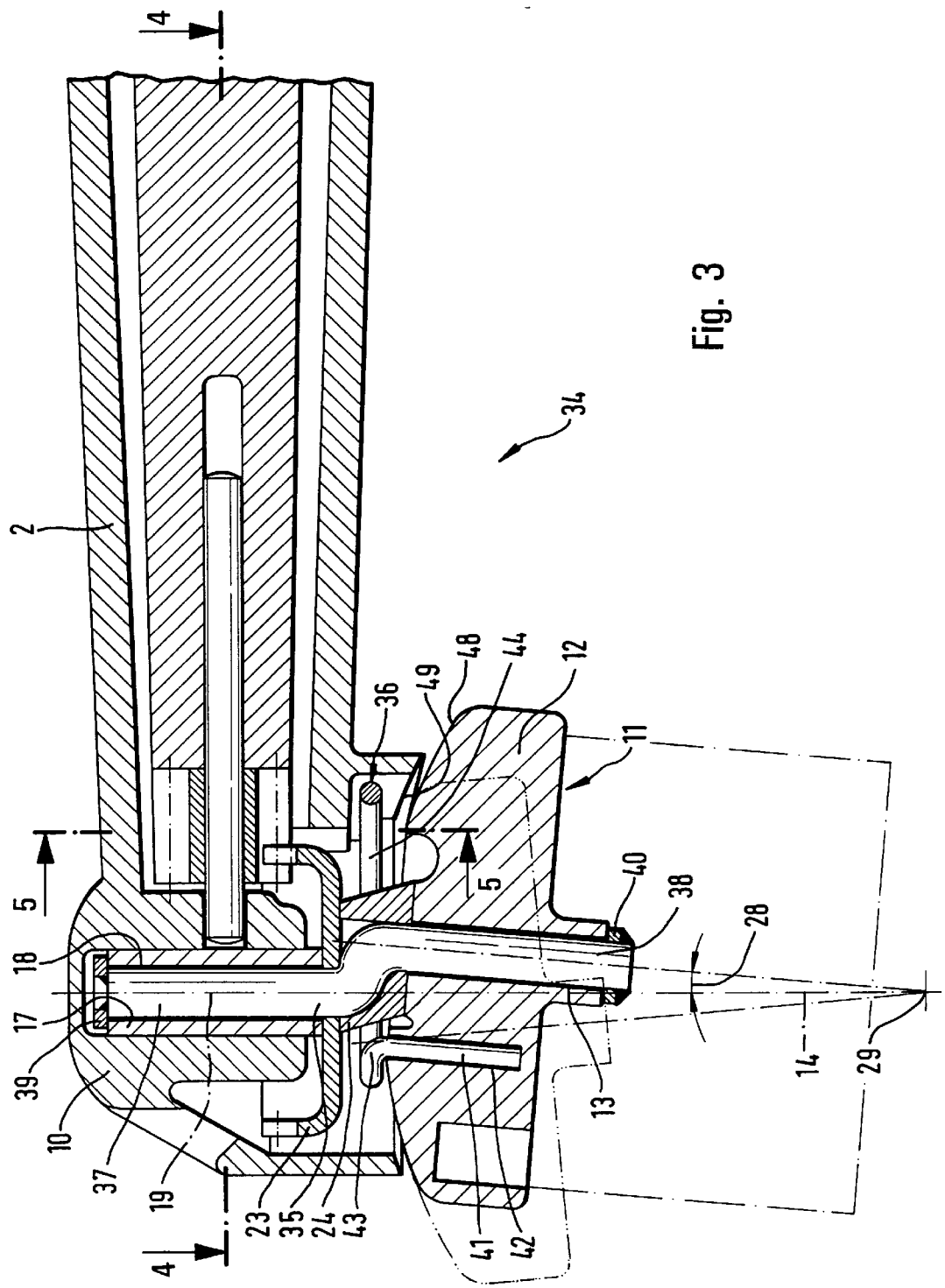

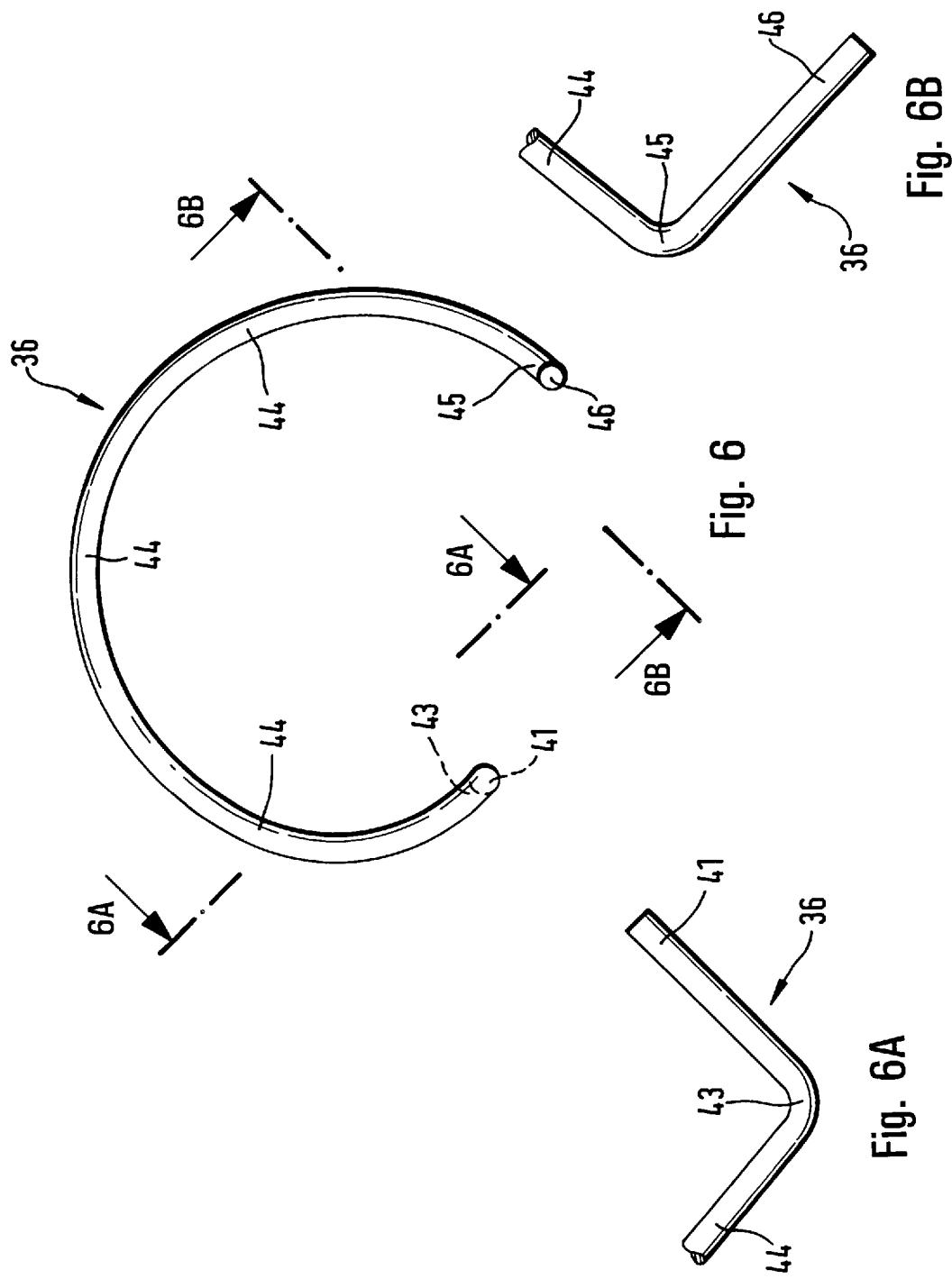

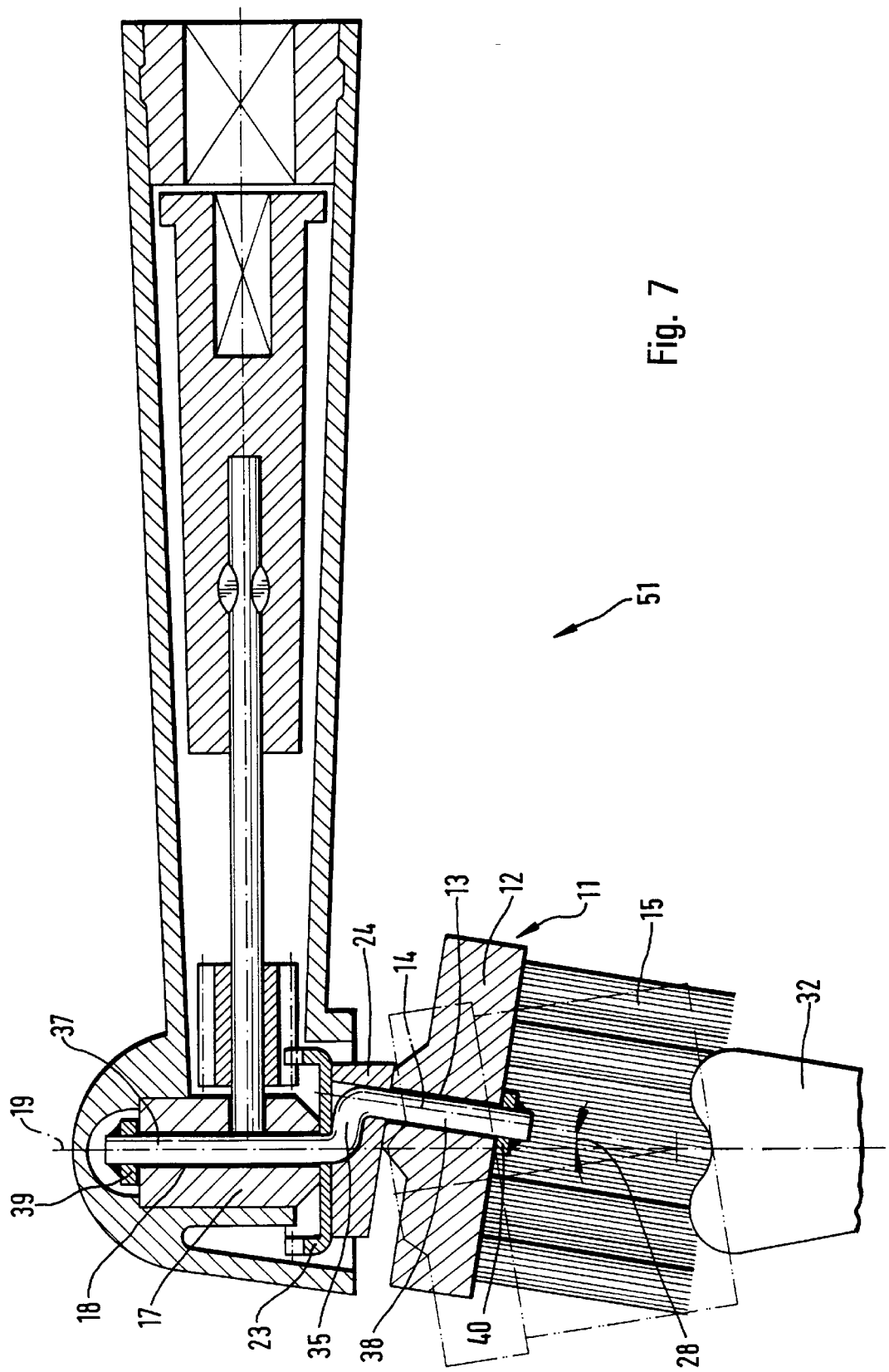

BRUSH SECTION FOR AN ELECTRIC TOOTHBRUSH

BACKGROUND OF THE INVENTION

This invention relates very generally to an electric toothbrush and particularly to a brush section for an electric toothbrush.

SUMMARY OF THE INVENTION

A brush section of this type is known from German Offenlegungsschrift DE 39 37 850 A1 which is hereby incorporated in the disclosure content of the present patent application by express reference. In this specification, an electric toothbrush is described which has a handle section from which a drive shaft projects outwardly. The handle section receives in its interior electric drive means with the aid of which the drive shaft can be set in an oscillatory rotational motion about its longitudinal axis. A brush section extending in the direction of the longitudinal axis and having a mounting tube with a bristle carrier arranged at its end is adapted to be push-fitted onto the handle section and the drive shaft. The mounting tube accommodates therein a shaft which, when push-fitted, is coupled to the drive shaft. Extending from the bristle carrier are bristles which are arranged approximately transversely to the longitudinal axis of the brush section. By means of a bevel gear arrangement, the oscillatory rotational motion transmitted by the drive shaft to the shaft of the brush section is deflected by about 90 degrees. As a result, with the electric toothbrush activated, the bristle carrier executes an oscillatory rotational motion about an axis which is approximately transverse to the longitudinal axis of the brush section. The cleansing face formed by the free ends of the bristles performs an equally oscillatory rotational motion on a user's tooth surfaces. This oscillatory rotational motion is apt to produce a good cleaning action on the tooth surfaces.

It is an object of the present invention to provide a brush section for an electric toothbrush with which an improved dental cleaning operation can be accomplished.

According to the present invention, this object is accomplished in a brush section for an electric toothbrush comprising a mounting tube, a shaft, and bristles extending from a bristle carrier, where the motion of the brush axis of the bristle carrier occurs on an envelope of a cone.

As a result of the nutating motion of the bristle carrier, that is, the movement of the brush axis on the envelope of a cone, the free ends of the bristles execute short approaching and receding motions in a direction more or less parallel to the bristles or the brush axis. This means that the free ends of the bristles are not continuously positioned against a user's tooth surfaces to be cleaned at a constant force, but are moved towards and away from the tooth surfaces alternately at a greater or smaller contact force, accordingly performing a kind of stroke. Experience has shown that such a movement of the brush is conducive to a significantly improved dental cleaning action. The user is not required to align the brush section relative to the tooth surfaces or in particular to the interproximal surfaces. Irrespective of the alignment, an improved cleaning action on the tooth surfaces including the interproximal surfaces is accomplished by the nutating motion. The approaching/receding motions of the free ends of the bristles further result in a very uniform cleaning action on the tooth surfaces, which is conducive to application by, and comfort for, the user. It is preferred that the movement of the brush axis be on the envelope of a circular cone, but it will be appreciated that other conical shapes with an elliptical or some other base may also be considered. Such modifications are within the scope of the present invention. Of importance is only that the bristles possess a component of motion in the direction of the surface normal of the tooth surfaces on account of their motion disclosed in the invention. Under circumstances, an additional, superimposed rotary or oscillatory motion of the brush about the brush axis may be dispensed with entirely, although a forced rotary motion of the brush about the brush axis may also be of advantage.

In an advantageous aspect of the present invention, the motion of the bristle carrier as disclosed in the invention is accomplished by the acute angle between the transverse axis and the brush axis. The brush axis and thus also the bristle carrier move on the envelope of a cone whose center axis is formed by the transverse axis. The nutating motion is thus produced in a simple way necessitating a low manufacturing effort.

In a particularly advantageous aspect of the invention, the apex of the cone lies inside the tooth when the brush head is engaged against the tooth. This has the effect that the approaching/receding motions performed by the free ends of the bristles envelope the tooth surfaces to be cleaned from all sides. In an advantageous alternative aspect of the invention, the apex of the cone may also lie outside the tooth, yet in the proximity of the tooth surface. Particularly suitably, the angle between the transverse axis and the brush axis is selected from the range of 2 to 14 degrees. In particular, an angle of about 6 to 3 degrees for an arrangement of the apex within the tooth, or an angle of about 10 to 5 degrees for an arrangement of the apex outside the tooth, have proven to be advantageous.

In a further aspect of the invention, the rotary motion of the shaft is converted simply by means of a pinion and a contrate gear into a rotary motion about the transverse axis. It will be understood, of course, that also other conversions are possible using, for example, a pair of bevel gears.

In an advantageous aspect of the invention, the pinion is connected with a bearing pin rotatably carried in the mounting tube. In a further aspect the contrate gear is connected with a tapered disk in which another bearing pin is held. In another aspect, this further bearing pin serves to rotatably mount the bristle carrier. In this arrangement, the first mentioned bearing pin is arranged in the transverse axis, and the second mentioned bearing pin is arranged in the brush axis, so that the two bearing pins define between them the acute angle equal to the acute angle between the transverse axis and brush axis. This configuration presents a simple and economical possibility to produce the nutating motion of the invention with few components.

In an alternative advantageous aspect of the invention, a bent shaft which may also be configured as a crankshaft is provided. In another aspect, this shaft has its one end rotatably carried in the mounting tube and its other end in the bristle carrier. A tapered disk may be arranged in-between. In this arrangement, the shaft is bent such that its two ends define between them the acute angle referred to above. It is in particular due to the use of the bent shaft that only few components are necessary which can be assembled together with ease. The configuration described is therefore very economical particularly with regard to the manufacture of the brush section.

In an advantageous further aspect of the invention, rotation of the bristle carrier is prevented from occurring. In consequence, only the nutating motion of the present invention, that is, the approaching/receding motions of the free ends of the bristles effect the cleaning of the tooth surfaces.

In another advantageous aspect, rotation of the bristle carrier is prevented by a groove extending in the mounting tube in the direction of the longitudinal axis, which groove is engaged by a finger of the bristle carrier. No further components are thus necessary, since rotation is prevented by a special configuration of the existing components.

In a further advantageous aspect, a retaining spring, a hinged lever or the like are provided to avoid rotation of the bristle carrier. These components have the advantage of ensuring that the nutating motion of the bristle carrier as disclosed in the invention is not impeded by friction, and that soiling, for example, with tooth paste residues, is of no consequence to the brush section's operating reliability. As a further advantage, the relative motion of the mounting tube and the bristle carrier which occurs as a result of the nutating motion is compensated for in a simple manner, that is, without particular provisions or some other particular effort.

A particularly straightforward configuration of the retaining spring is one in which the retaining spring includes two approximately right-angled portions as well as a spring portion in between. This particular retaining spring involves only low manufacturing cost. Moreover, it is particularly suitable to use a metal wire as retaining spring where two portions of the retaining spring are inserted in respective blind-end holes of the bristle carrier and mounting tube. This enables the retaining spring to be connected with the mounting tube and the bristle carrier simply by push-fitting.

In an advantageous further aspect of the invention, means are provided to produce a rotation of the bristle carrier. As a result, not only the nutating motion of the invention, that is, the approaching/receding motions of the free bristle ends contribute to cleaning the tooth surfaces, but in addition a rotary motion of the cleaning face formed by the bristles' free ends produces a cleaning action.

In another advantageous aspect, a rotation of the bristle carrier is produced by a mating bevel gear arrangement on the mounting tube and on the bristle carrier. The rotational frequency of this rotation, in particular with regard to the rotational frequency of the nutating motion of the invention, can be varied simply by suitably selecting the gear ratio of the bevel gearing.

If means are provided neither for preventing nor for producing a rotation of the bristle carrier, the bristle carrier may perform turning motions, in particular rotary or an oscillatory motions by reason of its rotary mounting, these motions being, however, uncontrolled and depending on the manner in which the user positions the bristles against the tooth surfaces.

In an advantageous further aspect of the invention, which may also be an independent invention, the relatively associated surfaces of the bristle carrier on the one side and the surfaces of the mounting tube as well as, where applicable, further necessary surfaces on the other side are domed in like manner. In particular it is especially suitable in a preferred embodiment to configure the surfaces referred to in spherical shape with a common sphere center. By virtue of this configuration, a constant distance results between the relatively associated surfaces of the mounting tube and the bristle carrier which is maintained also during movement. It is in particular by an arrangement of the sphere center in the apex according to another aspect of the invention that the relatively associated surfaces of the mounting tube and the bristle carrier are prevented from performing an opening and closing motion which could result in food residues or even parts of the user's skin being nipped.

In a further aspect of the invention, the invention may be implemented not only in the form of the brush section as such but also in the form of an electric toothbrush to which a suitable brush section is attached as, for example, by push-fitting.

Particularly advantageously, the electric toothbrush includes a continuously rotating drive mechanism. In this manner, a uniform revolving nutating motion of the bristle carrier is accomplished. In principle, it is however also possible to provide the electric toothbrush with an oscillatory drive mechanism.

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention.

BRIEF DESCRIPTION OF THE DRAWINGS

FIG. 2 is a schematic longitudinal sectional view of a brush section for an electric toothbrush utilizing a second embodiment of the invention;

FIG. 3 is a schematic longitudinal sectional view, taken along the plane 3—3 of FIG. 4, of a brush section for an electric toothbrush utilizing a third embodiment of the invention;

FIGS. 6, 6A, 6B are schematic longitudinal sectional views of the retaining spring utilized in the brush section of FIG. 3, illustrating three different views;

FIG. 7 is a schematic longitudinal sectional view of a brush section for an electric toothbrush utilizing a fourth embodiment of the invention.

DESCRIPTION OF THE PREFERRED EMBODIMENTS

The brush sections described in the following with reference to FIGS. 1 to 8 are suited to operate in conjunction with an electric toothbrush of the type disclosed in German Offenlegungsschrift DE 39 37 850 A1. According to the invention, however, the oscillatory drive mechanism set forth in the Offenlegungsschrift referred to may be replaced preferably by a continuously rotating drive mechanism, with both directions of rotation being possible. It will be appreciated, however, that the invention may be equally realized on the basis of an oscillatory drive of the electric toothbrush.

The electric toothbrush includes a handle section from which a drive shaft projects outwardly. The handle section accommodates in its interior electric drive means imparting rotation to the drive shaft about its longitudinal axis when activated. The drive shaft and that end of the handle section from which the drive shaft projects have their outer surfaces contoured for push-fitting engagement with a brush section and for transmission of the rotary motion produced.

Figure 1:
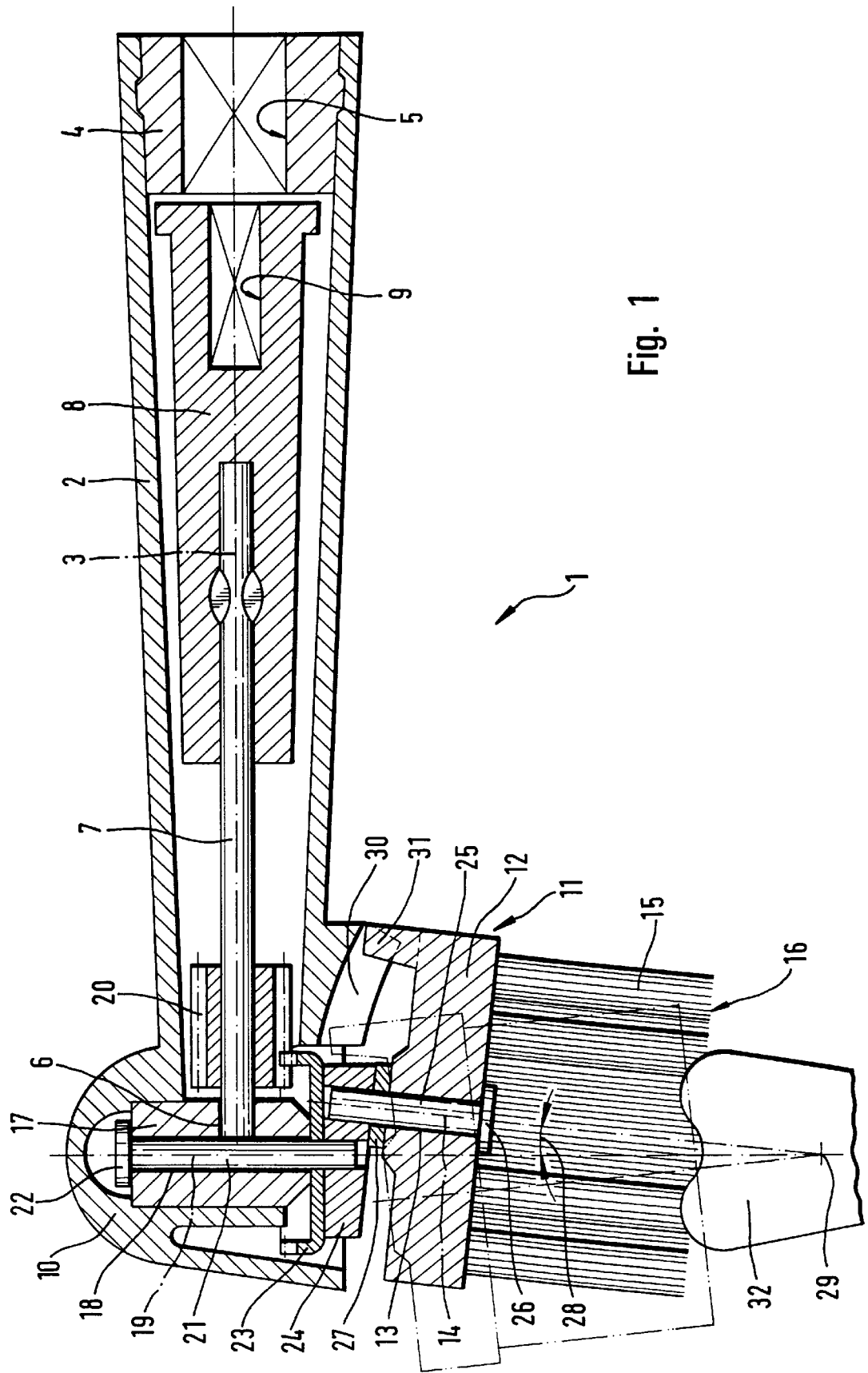
FIG. 1 is a schematic longitudinal sectional view of a brush section for an electric toothbrush utilizing a first embodiment of the invention.
Figure 5:
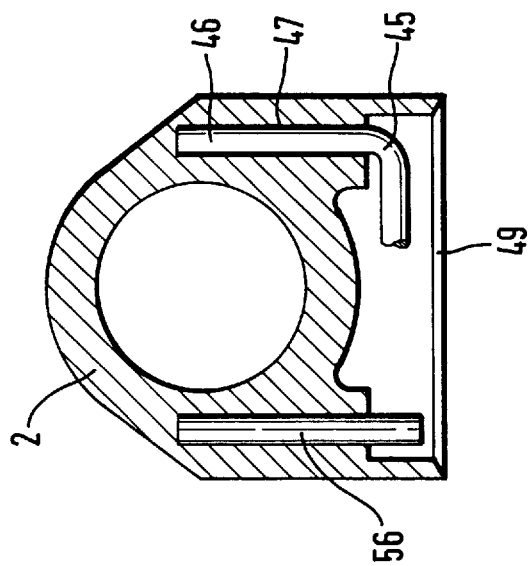
FIG. 5 is a schematic cross-sectional view, taken along the plane 5—5 of FIG. 3, of the brush section of FIG. 3.
Figure 4:
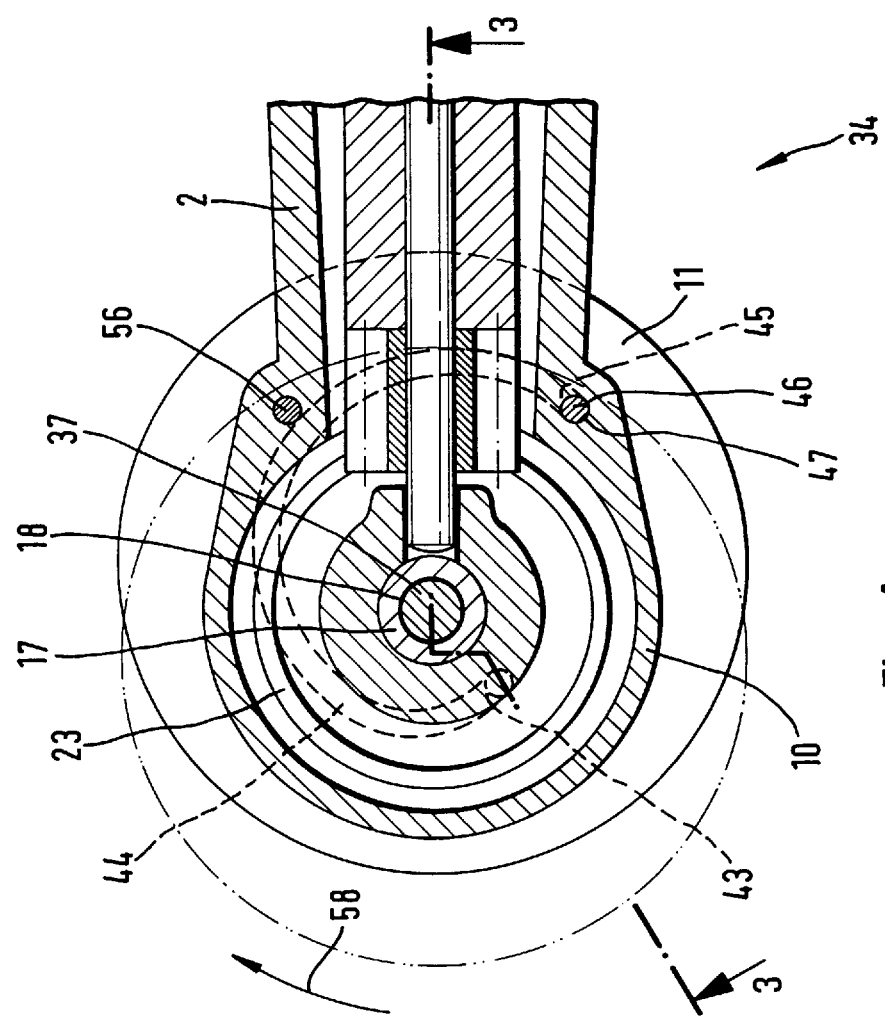
FIG. 4 is a schematic longitudinal sectional view, taken along the plane 4—4 of FIG. 3, of the brush section of FIG. 3.

FIG. 1 illustrates a brush section 1 which may be push-fitted onto the handle section and the drive shaft of the electric toothbrush referred to in the foregoing. The brush section 1 includes a mounting tube 2 extending in the direction of a longitudinal axis 3. At its free end close to the handle section, the mounting tube 2 has a profile ring 4 with an inside contour 5 complementary with the outside contour of the handle section. In this manner, the brush section 1 can be push-fitted onto the handle section in a manner preventing relative rotation.

At its end remote from the handle section, the mounting tube 2 has a bore 6 in which a shaft 7 is mounted for rotation. The shaft 7 is arranged in the longitudinal axis 3 of the mounting tube 2 and is preferably made of metal. The shaft 7 extends from the bore 6 in the direction close to the handle section approximately up to the center of the mounting tube 2. In the direction close to the handle section, the shaft 7 is fixedly coupled to another shaft 8 arranged in the longitudinal axis 3 and preferably fabricated from a plastic. The second shaft 8 has at its free end close to the handle section an inside contour 9 complementary with the outside contour of the drive shaft projecting outwardly from the handle section. This enables the drive shaft to be coupled to the second shaft 8 and thus also to the shaft 7 in a manner preventing relative rotation.

The inside and outside contours 5, 9 may be of a square, stellate or similar configuration when viewed in cross section, which are conformed to each other such as to enable a user to push and pull the brush section 1 onto and, respectively, off the handle section with ease, while at the same time a secure seat of the brush section 1 on the handle section is ensured.

At its end remote from the handle section, the mounting tube 2 has a cap structure 10. Further arranged in the area of this cap structure 10 are a bristle carrier 11 as well as means for coupling the bristle carrier 11 to the shaft 7 and to the mounting tube 2.

The bristle carrier 11 includes a disk-shaped plate 12 and a through-bore 13 and is essentially rotationally symmetrical to a brush axis 14. On its side facing away from the shaft 7, the plate 12 has a plurality of bristles 15 extending from the plate 12 in a direction approximately parallel to the brush axis 14. All of the bristles 15 are preferably of about equal length so that their free ends form an approximately circular cleansing face 16. The bore 13 in the plate 12 is in approximately parallel alignment with the brush axis 14, pointing approximately at the center of the cleansing face 16.

The bore 6 is provided in a bearing bush 17 which further includes a through bore 18 extending transversely to the bore 6. Accordingly, the bore 6 is aligned approximately parallel to the longitudinal axis 3, while the bore 18 is arranged approximately parallel to a transverse axis 19 extending at right angles to the longitudinal axis. The shaft 7 carried in the bore 6 does not extend into the area of the bore 18.

In the immediate vicinity of the bore 6, the shaft 7 carries a pinion 20 which is connected with the shaft 7 in a non-rotating relationship. It will be understood that a contrate gear, a bevel gear or the like may be provided in lieu of the pinion 20.

Rotatably mounted within the bore 18 is a bearing pin 21 which at its end remote from the bristle carrier 11 has a head or a disk 22 to capture the pin in the bore. A contrate gear 23 is non-rotatably fixed to the bearing pin 21 on the side of the bearing bush 17 close to the bristle carrier. This is accomplished, for example, by press-fitting the contrate gear 23 onto the bearing pin 21. The pinion 20 and the contrate gear 23 are in meshing engagement with one another. It will be appreciated that other components such as, for example, a bevel gear or the like, may be substituted for these gear components. Still further, a tapered disk 24 is connected with the bearing pin 21 in a non-rotating relationship, with the bearing pin 21 being, for example, a press-fit within the tapered disk 24 approximately in the center of said disk. The gear arrangement may be made of metal or plastic. In the latter case, the shafts 7, 8 and the pinion 20 as well as the contrate gear 23 and the tapered disk 24 are conveniently manufactured as an integrally formed injection molding.

Eccentrically to the bearing pin 21, a further bearing pin 25 is held in the tapered disk 24 in a rotationally fixed relationship thereto, for example by press-fitting. This bearing pin 25 serves to rotatably support the bristle carrier 11 by virtue of its being received in the bore 13 of the plate 12. The bearing pin 25 is thus arranged in the brush axis 14. At its end remote from the tapered disk 24, the further bearing pin 25 includes a disk 26 or a head for holding the bristle carrier 11 captured.

To reduce friction between the tapered disk 24 and the plate 12, the further bearing pin 25 carries a bearing washer 27 or the like between the components referred to. The bearing washer 27 may also be omitted.

The bearing pin 21 and thus the transverse axis 19 are disposed at approximately right angles to the surface of the tapered disk 24 facing them, while the further bearing pin 25 and thus the brush axis 14 are arranged at approximately right angles to the other surface of the tapered disk 24 facing them. The tapered disk 24 is thus configured such that its surfaces form an angle 28 with one other. As a result, the two bearing pins 21, 25 and accordingly the transverse axis 19 and the brush axis 14 equally form this particular angle 28 with one another. The angle 28 departs from an apex 29 in which the transverse axis 19 and the brush axis 14 intersect.

On the side of the mounting tube 2 close to the bristle carrier 11 is a groove 30 which, departing from the transverse axis 19, is disposed in the longitudinal direction. Still further, a finger 31 projecting from the bristle carrier 11 engages the groove 30 in which it is able to slide to and fro.

When the electric toothbrush is in operation, the drive shaft projecting outwardly from the handle section imparts a rotary or, where applicable, oscillatory motion about the longitudinal axis 3 to the shaft 7 and thus also to the pinion 20 of the brush section 1 push-fitted to the handle section. In consequence, the bearing pin 21 and the contrate gear 23 execute equally a rotary or oscillatory motion about the transverse axis 19. This causes the tapered disk 24 non-rotatably fixed to the contrate gear 23, and the further bearing pin 25 arranged in the brush axis 14 to be set in rotation or oscillation about the transverse axis 19. The bristle carrier 11 mounted on the bearing pin 25 likewise performs this motion about the transverse axis 19. Owing to the arrangement of the transverse axis 19 and the brush axis 14 at the angle 28, the bearing pin 25 and thus the brush axis 14 move on the envelope of a cone about the transverse axis 19. The opening angle of the envelope of the cone is double the value of the angle 28, the tip of the cone's envelope lying at the apex 29. Overall, therefore, the bristle carrier 11 performs a nutating motion about the transverse axis 19. This means that an approaching/receding motion is imparted to the free ends of the bristles 15 forming the cleansing face 16 of the bristle carrier 11, with the direction of these motions being essentially parallel to the bristles and thus approximately parallel to the brush axis 14. When a user positions the bristles 15 against a tooth 32 to be cleaned, the approaching/receding motions act in the direction of the surfaces of this particular tooth 32, ensuring a particularly effective cleaning action by removing plaque and the like from the teeth.

By engagement of the finger 31 within the groove 30, rotation of the bristle carrier 11 is avoided. During the nutating motion of the bristle carrier 11, the finger 31 performs a reciprocating motion inside the groove 30.

In the brush section 1 of FIG. 1, the angle 28 is approximately six degrees, preferably three degrees. The apex 29 lies approximately in the area of the tooth 32. In this manner, complete coverage of the tooth surfaces to be cleaned is ensured by the approaching/receding motions of the bristles 15.

In contrast thereto, the angle 28 in the brush section 33 of FIG. 2 is approximately ten degrees, preferably five degrees. In this embodiment, an apex 29 lies outside, yet in the vicinity, of the tooth 32.

The brush section 34 illustrated in FIGS. 3 to 6 differs from the brush sections 1, 33 described with reference to FIGS. 1 and 2 in the following significant points. First, a bent shaft 35 substitutes the two bearing pins 21, 25, and furthermore a retaining spring 36 is provided in lieu of the groove 30 and the finger 31. It will be understood, of course, that other components as, for example, hinged levers, strings or other elastomer parts may be utilized as well.

According to FIG. 3, the shaft 35 has a section 37 which is arranged in the bore 18 of the bearing bush 17 in the transverse axis 19 where it is rotatably carried. This section 37 of the shaft 35 supports the contrate gear 23 which is connected with the shaft 35 in a non-rotating relationship. The bent section of the shaft 35 is disposed in the area of the tapered disk 24, such as to connect the tapered disk with the shaft 35 in an equally non-rotating relationship. Moreover, the shaft 35 has a section 38 which is arranged in the bore 13 of the plate 12 in the brush axis 14 where it is rotatably carried. The two free ends of the shaft 35 are provided with respective disks 39, 40 holding the shaft captured. The shaft 35 is preferably fabricated from a bent piece of round metal.

By virtue of the bent configuration of the shaft 35, the two sections 37, 38 define between them the angle 28 as a result of which the bristle carrier 11 performs a kind of wobbling motion, that is, a nutating motion, when in operation.

The retaining spring 36 is made of a piece of metal wire connecting the bristle carrier 11 with the mounting tube 2. The shape of the retaining spring 36 becomes clear in particular when looking at the FIGS. 3 to 6 jointly. Thus it appears in particular from FIG. 3 that a portion 41 of the retaining spring 36 is inserted in a blind-end bore 42 in the plate 12 of the bristle carrier 11. As shown in particular in FIG. 6, there follows then an approximately right-angled bight portion 43 following which the retaining spring 36 merges into a spring portion 44. According to FIGS. 4 and 6, this spring portion is of an arcuate shape with varying radius. Provided at the other end of the spring portion 44 is an approximately right-angled bight portion 45, such that the subsequent portion 46 points in a direction opposite the portion 41. This becomes apparent in particular from FIGS. 5 and 6. According to FIG. 5, the portion 46 is received in a blind-end bore 47 of the mounting tube 2. A cylindrical pin 56 is press-fitted into the mounting tube 2 approximately symmetrically to the blind-end bore 47.

In operation, the bristle carrier 11 is set in a wobbling, that is, nutating motion. When the shaft 35 rotates in a direction 58, the retaining spring 36 bears against the cylindrical pin 56. In this manner, rotation of the bristle carrier 11 is prevented by reason of the connection of the bristle carrier 11 with the mounting tube 2 via the retaining spring 36. The movements of the bristle carrier 11 relative to the mounting tube 2 are compensated for by elastic twisting and/or bending deformation of particularly the spring portion 44 of the retaining spring 36. It will be understood, of course, that the press-fitted cylindrical pin 56 may be replaced by a stop integrally formed on the mounting tube 2 or similar structural approaches.

Another difference between the brush section 34 of FIGS. 3 to 6 and the brush sections 1, 33 of FIGS. 1 and 2 resides in the configuration of the relatively associated surfaces of the bristle carrier 11 and the mounting tube 2. As appears particularly from FIG. 3, a surface 48 of the plate 12 of the bristle carrier 11 on the side close to the mounting tube 2 is of a spherical configuration, the sphere having its center in the apex 29. Further, a surface 49 of the cap structure 10 of the mounting tube 2 on the side close to the bristle carrier 11 is of a spherical configuration, with the center of the sphere being likewise in the apex 29. As a result, a constant distance is obtained between the facing surfaces 48, 49 which is maintained unchanged also under operating conditions, that is, during a nutating or wobbling motion of the bristle carrier 11.

It will be appreciated that the adaptation of the relatively associated surfaces 48, 49 of the bristle carrier 11 and the mounting tube 2 and the cap structure 10 as described in connection with the brush section 34 of FIG. 3 can be performed also with the brush sections 1, 33 of FIGS. 1 and 2. The same applies to the brush sections 51, 52 described in the following with reference to FIGS. 7 and 8. It will be further appreciated that the adaptation referred to may also involve an invention in its own right, independently of the other features of the brush sections 1, 33, 34, 51, 52.

Differing from the brush sections 1, 33, 34 of FIGS. 1 to 6, the brush section 51 illustrated in FIG. 7 possesses no means for preventing rotation of the bristle carrier 11. Accordingly, there is neither a groove 30 engaged by a finger 31, nor a retaining spring or the like. In consequence, friction occurring in operation between the plate 12 and the tapered disk 24 imparts a rotary motion to the bristle carrier 11 about the section 38 of the shaft 35 and thus about the brush axis 14. When the user engages the bristles 15 against the tooth 32 for cleaning, this rotation of the bristle carrier 11 is slowed down by the frictional engagement with the tooth 32. Any residual rotation then depends on the pressure at which the user positions the bristles 15 against the tooth 32. By applying a fairly high pressure, the user may practically eliminate rotation completely. Overall, in operation, there results with the brush section 51 of FIG. 3 a nutating motion having superposed on it a free or uncontrolled rotation of the bristle carrier 11 whose frequency is dependent on the contact pressure exerted by the user.

Figure 8:
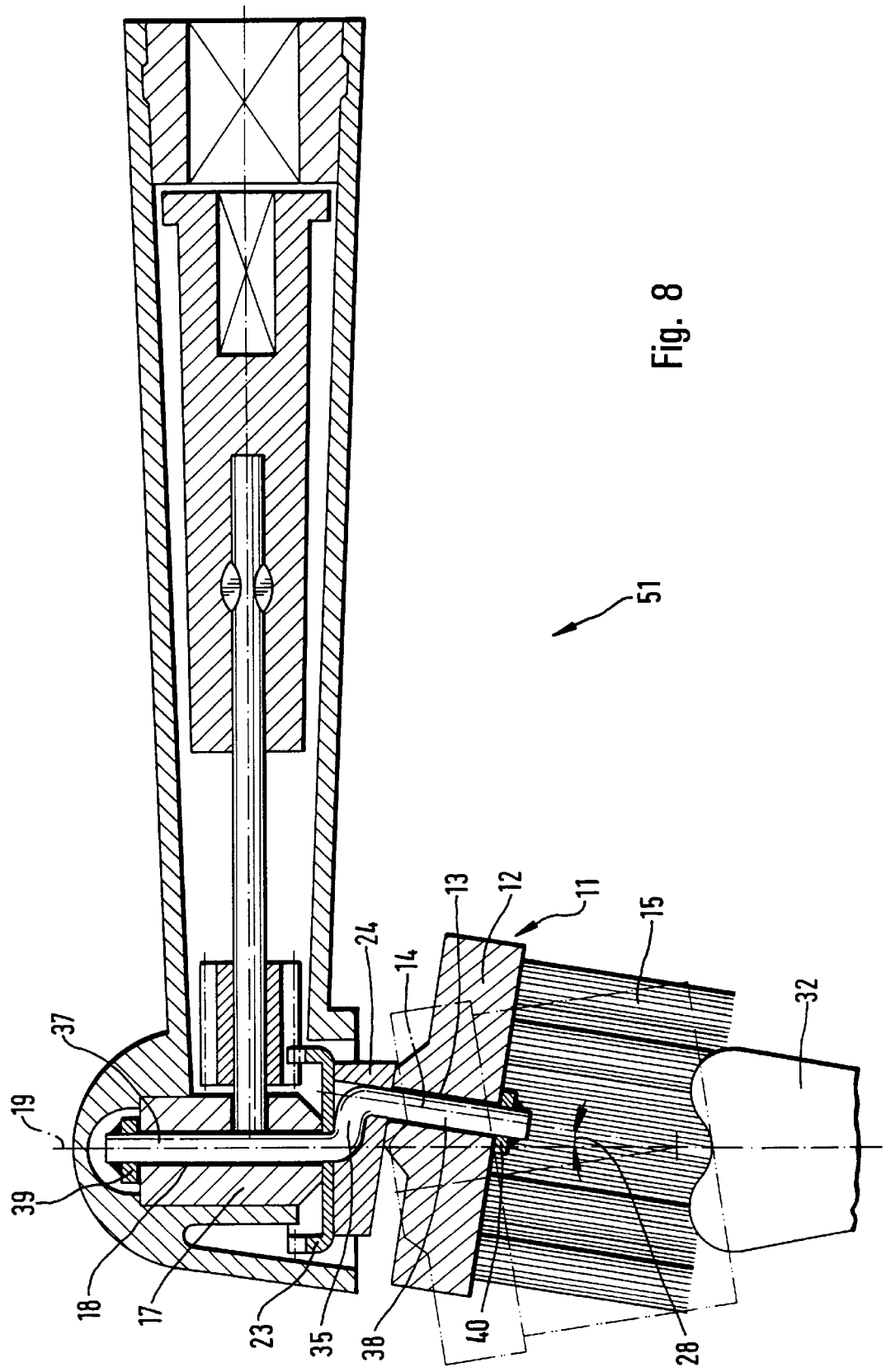
FIG. 8 is a schematic longitudinal sectional view of a brush section for an electric toothbrush utilizing a fifth embodiment of the invention.

Rather than possessing means for preventing rotation of the bristle carrier 11, the brush section 52 illustrated in FIG. 8 includes means for producing such rotation. In contrast to the brush sections of FIGS. 1 to 6 in which rotation is not possible, and the brush section 51 of FIG. 7 in which a free or uncontrolled rotation is possible, the brush section 52 of FIG. 8 enables a controlled or forcibly controlled rotation of the bristle carrier 11.

To accomplish this, a bevel gearing 53 rotary through 360 degrees is provided on the outer periphery of the plate 12 on the side of the bristle carrier 11 close to the mounting tube 2. Further, another bevel gearing 54 equally rotary through 360 degrees is provided on the side of the mounting tube 2 and the cap structure 10 close to the bristle carrier 11. The two bevel gearings 53, 54 are in meshing engagement with one another, with the engagement of the bevel gearings 53, 54 being rotating.

In operation, the bristle carrier 11 executes a nutating motion. At the same time, the two bevel gearings 53, 54 operate to produce rotation of the bristle carrier 11 about the brush axis 14. The rotational frequency of this rotation depends on the gear ratios of the two bevel gearings 53, 54.

We claim:

1. A brush section for an electric toothbrush, comprising:
   a mounting tube;
   a shaft within said mounting tube and rotary about a longitudinal axis;
   a bristle carrier having a brush axis and bristles extending therefrom and being rotary about a transverse axis and coupled to said shaft; and
   a coupling mechanism connecting said bristle carrier to the shaft and which converts a rotational motion of the shaft about the longitudinal axis to a motion of the bristle carrier (11) and the brush axis relative to the transverse axis, whereby the motion of the brush axis of the bristle carrier occurs essentially on an envelope of a cone.

2. The brush section as claimed in claim 1, wherein the transverse axis and the brush axis define between them an acute angle about an apex.

3. The brush section as claimed in claim 2, wherein the apex lies at a distance from the bristle carrier beyond a surface defined by distal ends of the bristles when the bristles are in use.

4. The brush section as claimed in claim 2, wherein the apex lies at a distance from the bristle carrier before a surface defined by distal ends of the bristles when the bristles are in use.

5. The brush section as claimed in claim 2 wherein the acute angle has a value in a range of approximately 2 to 14 degrees.

6. The brush section as claimed in claim 2, wherein the acute angle has a value in a range of approximately 6 to 10 degrees.

7. The brush section as claimed in claim 2, wherein the acute angle has a value in a range of approximately 3 to 5 degrees.

8. The brush section as claimed in claim 1, wherein said coupling mechanism comprises:
   a first gear carried by the shaft, said first gear connected with said shaft in a non-rotating relationships; and
   a second gear rotary about the transverse axis, said second gear being in meshing engagement with said first gear and coupled to said bristle carrier.

9. The brush section as claimed in claim 8, wherein said coupling mechanism comprises:
   a bearing pin rotatably carried in the mounting tube, said bearing pin being connected with said second gear in a non-rotating relationship.

10. The brush section as claimed in claim 9, wherein said coupling mechanism comprises:
    a second bearing pin, wherein the bristle carrier is rotatably mounted on said second bearing pin.

11. The brush section as claimed in claim 8, wherein said coupling mechanism comprises:
    a bent shaft fabricated from a bent piece of round metal, said shaft having a section thereof connected with said second gear in a non-rotating relationship and being rotatably carried in the mounting tube.

12. The brush section as claimed in claim 11, wherein the bristle carrier is rotatably mounted by means of a section of said bent shaft.

13. The brush section as claimed in claim 8, wherein the coupling mechanism comprises:
    a tapered disk, wherein the bristle carrier is connected with said second gear through said tapered disk.

14. The brush section as claimed in claim 8, wherein said first gear is a pinion.

15. The brush section as claimed in claim 8, wherein said second gear is a contrate gear.

16. The brush section as claimed in claim 1 further comprising:
    means to prevent rotation of the bristle carrier about the brush axis.

17. The brush section as claimed in claim 16, wherein the mounting tube includes a groove extending radially to the brush axis; and said means for preventing rotation of the bristle carrier comprises:
    a finger protruding from the bristle carrier and engaging said groove.

18. The brush section as claimed in claim 16, wherein said means for preventing rotation of the bristle carrier is a retaining spring.

19. The brush section as claimed in claim 18, wherein said retaining spring includes:
    two approximately right-angled portions; and
    a spring portion connecting said right-angled portions.

20. The brush section as claimed in claim 19, wherein said retaining spring is made of a piece of metal wire, and where said bristle carrier and said mounting tube each have blind-end holes, wherein said right-angled portions of the retaining spring are inserted in the blind-end holes of said bristle carrier and said mounting tube.

21. The brush section as claimed in claim 1 further comprising:
    means to produce a rotation of the bristle carrier about the brush axis.

22. The brush section as claimed in claim 21, wherein said rotating means comprises:
    a first bevel gearing on the mounting tube; and
    a second bevel gearing on the bristle carrier wherein said first and second bevel gearings are in meshing engagement with one another.

23. The brush section as claimed in claim 1, wherein said mounting tube and bristle carrier have relatively associated surfaces which are domed in a complementary manner.

24. The brush section as claimed in claim 23, wherein said mounting tube comprises:
    a cap structure having a surface relatively associated with a surface of said bristle carrier, wherein the relatively associated surfaces of said bristle carrier, and said cap structure are of a spherical configuration and have a common sphere center.

25. The brush section as claimed in claim 24, wherein the common sphere center is the apex of an acute angle of defined by the transverse axis and the brush axis.

26. The brush section as claimed in claim 23, wherein the relatively associated surfaces of said bristle carrier and said mounting tube are of a spherical configuration and have a common sphere center.

27. The brush section as claimed in claim 26, wherein the common sphere center is the apex of an acute angle defined by the transverse axis and the brush axis.

28. An electric toothbrush having a brush section as claimed in claim 1.

29. The electric toothbrush as claimed in claim 28, comprising:
    a continuously rotating drive mechanism.

* * * * *